United States Patent [19]

Tscherter et al.

[11] Patent Number: 4,753,959
[45] Date of Patent: Jun. 28, 1988

[54] ANTIBIOTIC LACTONE COMPOUND

[75] Inventors: Hans Tscherter, Allschwil; Hans Hofmann, Ettingen; Roy Ewald, Binningen; Michael M. Dreyfuss, Basel, all of Switzerland

[73] Assignee: Sandoz Ltd., Basel, Switzerland

[21] Appl. No.: 936,196

[22] Filed: Dec. 1, 1986

Related U.S. Application Data

[63] Continuation of Ser. No. 853,085, Apr. 17, 1986, abandoned, which is a continuation of Ser. No. 699,915, Feb. 8, 1985, abandoned.

[30] Foreign Application Priority Data

Feb. 8, 1984 [DE] Fed. Rep. of Germany ....... 3404399

[51] Int. Cl.$^4$ ........................................... C07D 407/04
[52] U.S. Cl. .................... 514/460; 549/292; 435/118
[58] Field of Search ..................... 549/292; 514/460

[56] References Cited

FOREIGN PATENT DOCUMENTS 1171424 7/1984 Canada ............................... 549/292

Primary Examiner—Jane T. Fan
Attorney, Agent, or Firm—Gerald D. Sharkin; Robert S. Honor; Thomas O. McGovern

[57] ABSTRACT

The compound of formula I

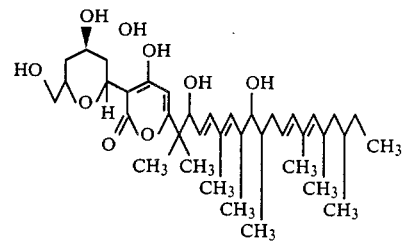

known as S 39163/F-I which is effective e.g. as an antimicrobial and against herpes viruses.

4 Claims, 3 Drawing Sheets

ANTIBIOTIC LACTONE COMPOUND

This is a continuation of application Ser. No. 853,085, filed Apr. 17, 1986 now abandoned, which in turn is a continuation of application Ser. No. 699,915, filed Feb. 8, 1985, now abandoned.

Figure 1:
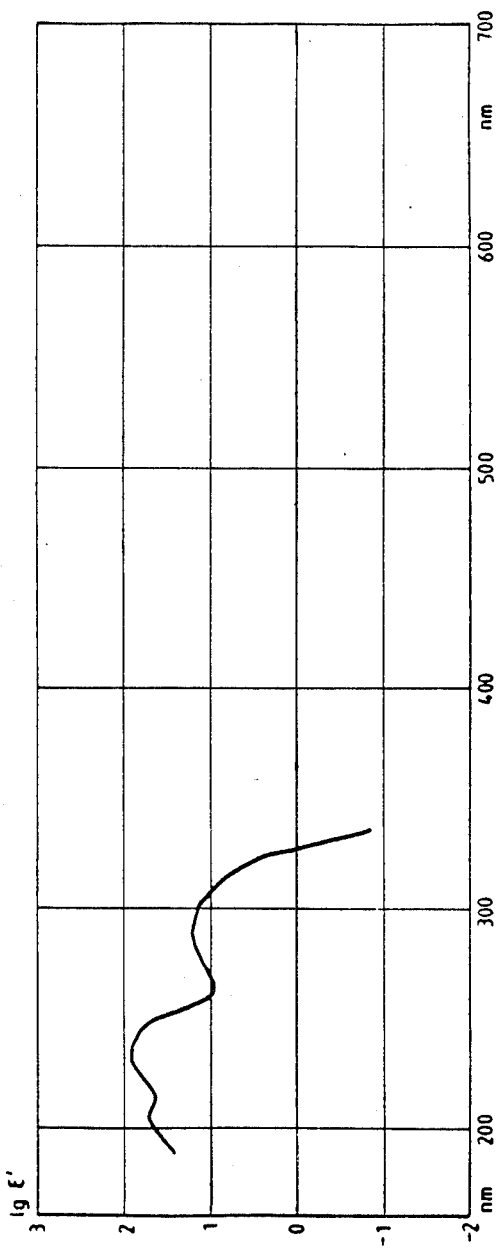
Figure 2:
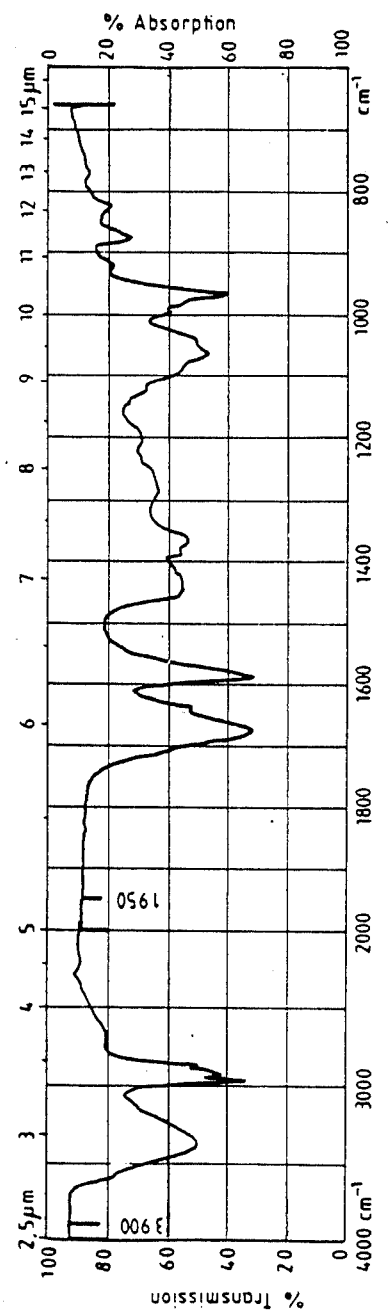
Figure 3:
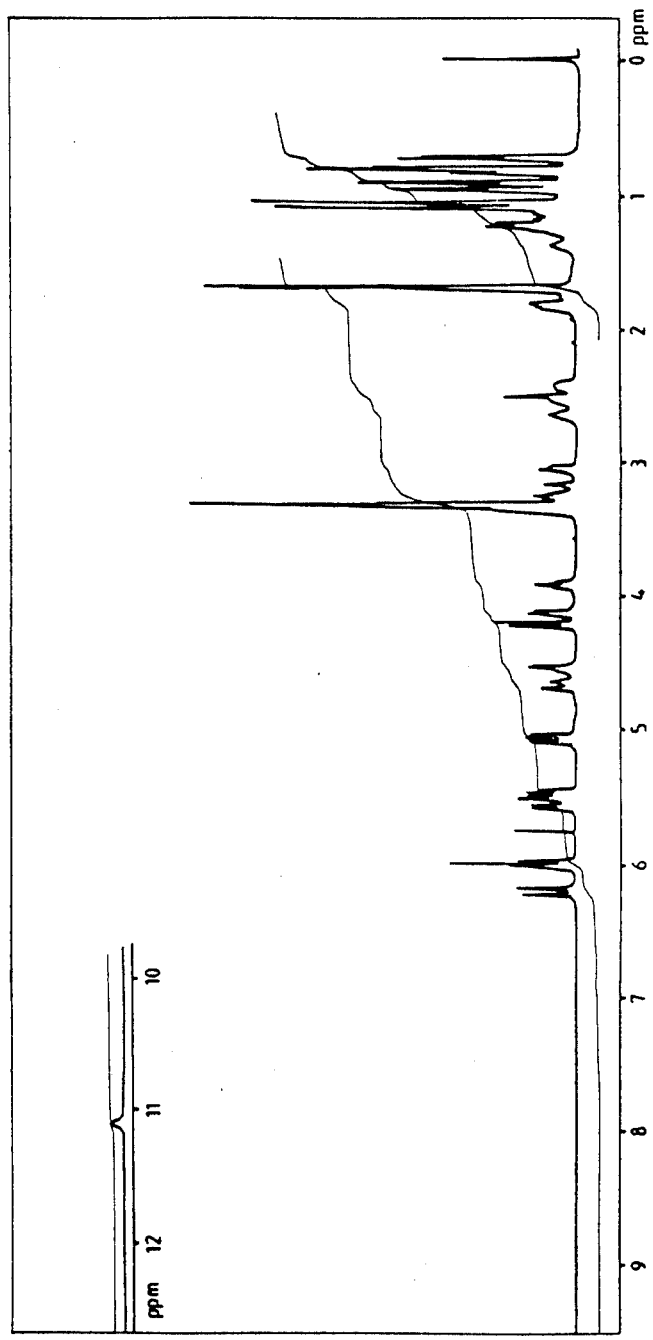

The present invention relates to the compound of formula I in free form or in the form of its alkali salts (the compound of formula I is referred to hereinafter as S 39163/F-I). S 39163/F-I in free form or in the form of its alkali salts is obtained in accordance with the invention by culturing a S 39163/F-I producing strain especially of the genus Microsphaeropsis Hohn in the presence of a culture medium and recovering S 39163/F-I in free form or in the form of an alkali salt. The Metabolite S 39163/F-I has the following approximate characteristics:

Colourless amorphous powder
M.p. 105°–115° sintering, from 124° decomp.
$[\alpha]_D^{20} = -15°$ (=0.50 in methanol)
Mol. weight according to field desorption mass spectrum: 660
Empirical formula: $C_{38}H_{60}O_9$ (660.9)
Analysis: found C, 68.5; H, 9.1; O, 22.66%. calc. C, 69.1; H, 9.1; O, 21.86%.
UV spectrum in methanol: Max. 205 nm, log $\epsilon'1.69$; 235 nm, log $\epsilon'1.90$; 290 nm, log $\epsilon'1.18$; (compare FIG. 1)
IR spectrum $CH_2Cl_2$ (compare FIG. 2)
$^1$H-NMR spectrum in dimethylsulphoxide, 360 MHz with tetramethylsilane as internal standard (compare FIG. 3)
Solubility: S 39163/F-I is readily soluble in chloroform, ethanol, methanol, pyridine, dimethylsulphoxide, and poorly soluble in ether, hexane, water.
Stability: S 39163/F-I as an amorphous powder can be stored at $-20°$ over a long period of time without any noticeable decomposition. A 1% solution in 1-N $NaHCO_3$-ethanol (9:1) is stable at room temperature for 48 hours. A 2% solution in 0.05-M $K_2CO_3$ solution in methanol-water (9:1) proved to be stable according to thin-layer chromatographic analysis after 4 days at room temperature.

The following table gives the $R_f$ values of S 39163/F-I according to thin-layer chromatography (silica gel Merck 60 F 254-plates, 0.25 mm layer thickness, travelling distance 12 cm).

| Eluant | $R_f$ values S 39163/F-I |
|---|---|
| methylene chloride-methanol-water (70:25:4) | 0.28 |
| toluene-isopropanol-water (50:50:5) | 0.21 |
| methanol-methylene chloride | 0.34 |
| (30:70) | |

Iodine can be used as the detection reagent. Upon spraying with a 0.1% $FeCl_3$ solution in acetic acid—conc. sulphuric acid (1:99), S39163/F-I produces a yellow spot; after heating to 120°, a brown colouring appears.

HPLC Analysis of S 39163/F-I
  Column material: Li-Chrosorb RP 8 ®R Merck (fine silica gel)
  Mobile phase: triethylamine-phosphate buffer pH 4.5/acetonitrile (50:50)
  Retention time: 7.3 mins. flow speed 2 ml/min.
  Detection: UV 290 nm The process according to the invention may be carried out using known methods. A subculture of the strain producing the metabolide S 39163/F-I was deposited at the United States Department of Agriculture (North Central Region, Northern Regional Research Center), Peoria, Ill., USA, on Oct. 3, 1983, from which it is available to the public under the number NRRL 15684. This culture can also be obtained from Sandoz AG, Basle, Switzerland.

Characteristics of the strain NRRL 15684

The fungus strain NRRL 15684 was isolated from the leaftissue of Buxus sempervirens L. Under certain cultur conditions, the fungus strain develops dark brown, globose, separate pycnidia which are 200–500μ (usually 250–350μ) in diameter and are superficial or immersed in the agar, and usually have one, sometimes 2-3 papillate ostioles. As far as can be judged by light microscopy, the light-brown, oval to cylindrical, thin-walled condidia, 4–6×2-3μ (usually 5×2.5μ) in size are produced by phialides. The phialides measuring 5–7×-7-7.5μ are globular to pyriform with a short extended periclinal region.

According to the morphological features and by using the diagnostic keys of B. C. Sutton (in: The Coelomycetes; Commonwealth Mycological Institute, Kew, Surrey, England 1980), the fungus strain NRRL 15684 can be assigned to the genus Microsphaeropsis Höohn.

The following physiological features are characteristics of the fungus strain NRRL 15684 (The following culture media were used to characterise the fungus strain):

MA: 2% Difco malt extract; 0.4% Difco yeast extract, 2% Difco Agar.
CM: Difco corn-meal-Agar.
PA: 0.5% pure soya protein (Promine D), 0.1% Difco yeast extract, 2% Difco Agar. Clearing the medium indicates protein degradation.
SA: 0.4 g soluble starch (Difco), 0.1% Difco yeast extract, 2% Agar Starch degradation can be demonstrated by flooding with KJ solution.
CAA: Cellulose-Azure (Calbiochem)-test by R. E. Smith 1977: Applied and Environmental Microbiology 33, (4), 980
TA: Tween 40-medium by G. Sierra 1957: Antonie von Leeuwenhoek 23; 15–22. Medium turbidity indicates lipase activity.
Media with pH 2.6 to pH 4.0: MA-medium buffered with 0.1 M citric acid/0.1 M $Na_2HPO_4$-buffer according to McIlvaine in: Data for Biochemical research, Oxford, 1969, pages 484–485.

Media with pH 9.2–10.0: MA-medium buffered with 0.1 M NaCO$_3$/0.1 M NaHCO$_3$ buffer according to Delory and King in: Data for Biochemical Research, Oxford 1969, page 496.

The buffers and the media are sterilised separately and combined after sterilisation.

Physiological features of the strain NRRL 15684

The optimum growth temperature of the strain NRRL 15684 is around 21° C. (between 18° and 24° C.). On MA at 21° C., the colonies attain a diameter of 45–53 mm after 7 days. The upper growth limit lies between 30° and 33° C., and the lower growth limit is ca. 0° C.

On MA, a velvety to floccose aerial mycelium is produced, which is initially white, later becoming buff to grey. The underneath of the colony has a light honey-brown appearance. On CM, a completely colourless, sparce substrate mycelium develops. The pycnidia are produced both on MA and on CM, preferably in radial sectors. Light, e.g. daylight, promotes the formation of pycnidia.

The strain NRRL 15684 breaks down protein (PA), starch (SA) and cellulose (CAA), while no lipase activity (TA) was detected.

At a pH of 2.6, the growth of the fungus strain is considerably slower than at a pH of 4; at a pH of 9.2, the mycelial growth is retarded to a great extent and at a pH of 10, growth is practically completely inhibited.

The new strain NRRL 15684 may be cultured at suitable temperatures in various culture media using appropriate nutrients and mineral substances, as aerobic surface or immersion cultures. The invention also concerns fermentation broths which are obtained during the cultivation of the S 39163/F-I producing strains of Microsphaeropsis Höohn. The metabolite S 39163/F-I formed is subsequently recovered in free form or in the form of an alkali salt. The fermentation media should mainly contain an utilisable source of carbon and optionally mineral salts and growth factors, whereby all these elements can be added in the form of well defined products or complex mixtures, as are found in biological products of various origins.

In order to produce the new metabolite S 39163/F-I, strains may also be used which are obtained e.g. by selection or mutation under the influence of ultra-violet rays or X-rays, or using other means, e.g. by treating cultures with appropriate chemicals. As soon as a sufficient amount of S 39163/F-I has been produced in the culture which may e.g. be ascertained e.g. by the activity towards Candida tropicalis or Aspergillus niger or by thin-layer chromatography, the mycelium may be separated from the culture broth and extracted in conventional manner, e.g. with an organic solvent which is immiscible in water, such as ethyl acetate, butyl acetate or n-butanol. Another isolation procedure comprises first homogenising the mycelium portion in the culture broth, e.g. using an Ultraturrax, and obtaining the metabolite by extraction with the solvents mentioned. A preferred embodiment comprises separating the culture broth into mycelium and culture filtrate by by centrifugation and/or filtration. The mycelium filtrate is then extracted with methanol or with acetone by homogenising with a Turrax, the cell material is centrifuged off and the organic phase is concentrated on water, whilst adding water. Here again extraction is effected with an organic solvent which is immiscible with water, e.g. ethyl acetate or n-butanol, and the extracts are evaporated under vacuum, preferably at 40°–50° C. The portion of active substance remaining in the culture filtrate can also be extracted using the solvents mentioned above.

S 39163/F-I can be isolated and puified from the crude extracts thus obtained by known chromatographic methods.

It has proved advantageous to first scour the crude extracts using hexane or petroleum ether to remove lipophilic impurities S 39163/F-I can then be isolated by gel filtration on Sephadex LH 20, followed by repeated chromatography on silica gel.

S 39163/F-I can be also converted to the corresponding alkali salts by reaction with suitable alkali metal bases. Such salts are e.g. sodium, potassium or lithium salts.

S 39163/F-I and its pharmaceutically acceptable alkali salts are useful as pharmaceuticals.

S 39163/F-I is antimicrobially active; in particular, the growth of yeast and hypomycetes is inhibited. In the agar diffusion test, no activity against bacteria was observed.

In series dilution tests the following minimal inhibitory concentrations were observed (mcg/ml):

| organism | S 39163/F-I |
|---|---|
| Candida krusei | 6.25 |
| Candida tropicalis | 6.25 |
| Candida albicans | 12.5 |
| Trichophyton quinckeanum | 6.25 |
| Aspergillus fumigatus | 1.56 |
| Aspergillus niger | 1.56 |

Sabourand Maltose, inoculum density 10$^5$ organisms/ml, incubation temperature 37° C., over 24 hours.

The metabolite S 39163/F-I has interesting biological properties and can therefore be used as a medicament.

Furthermore, the Metabolite S 39163/F-I has a marked effect on herpes viruses, as exhibited in vitro and in vivo tests. The activity was indicated by a reduction in the cytopathogenic effect (CPE), using various viruses, e.g. of Herpes simplex I and II, in vitro, from a concentration fo about 3 μg/ml to about 300 μg/ml.

For the above mentioned uses the dosage will of course vary depending on the compound employed, mode of administration and condition to be treated. With larger mammals, satisfactory results are in general obtained when administered ca. 7 to 15 mg/kg animal body weight e.g. at a daily dosage of 500–1000 mg, especially ca. 700 mg conveniently given in divided doses two to four times daily (e.g. for oral use containing ca. 125–500 mg) or in sustained release form. S 39163/F-I can be used in a similar manner and at similar dosages to preparations known for this purpose, e.g. Acyclovir.

Metabolite S 39163/F-I can be used in free form or in the form of a pharmaceutically acceptable alkali salt such as the sodium salt.

The invention also concerns a method of treating diseases and infections caused by microbes and herpes viruses which comprises administering to a subject in need of such treatment S 39163/F-I in free form or in the form of a pharmaceutically acceptable alkali metal salt, and pharmaceutical compositions containing an effective amount of S-39163/F-I in free form or in pharmaceutically acceptable alkali salt form in association with a pharmaceutically acceptable diluent or carrier.

The compounds may be administered preferably orally or parenterally suitably in admixture with conventional pharmaceutically acceptable diluents and carriers, and, optionally, other excipients.

Such compositions also form part of the invention.

In the following Examples, which illustrate the execution of the process more fully, but in no way limit the scope of the invention, all temperatures are given in degrees celsius.

EXAMPLE 1

CULTIVATION OF STRAIN NRRL 15684 IN AN AGITATED FLASK (a) Innoculum production 200 ml of medium 85 (composition and preparation: malt extract 20 g/l; yeast extract 4 g/l; pH 5.6–5.8 prior to sterilisation; sterilisation 20 minutes at 120°) are inoculated in a 500 ml Erlenmeyer flask with mycelium (from agar) of the strain NRRL 15684, and incubated at 24° in an agitating machine at 220 rpm.

After the culture has grown (3–5 days), there are placed in punctiform on the surface of 50 ml of Corn-Agar (composition and preparation: Bacto Cornmeal Agar 17 g/l; pH 6.5 prior to sterilisation; sterilisation for 20 minutes at 120°) into a 200 ml Erlenmeyer flask. Incubation takes place for 17 days at 24°, whereby the cultures are subjected to day-night cycles.

(b) Preculture 200 ml Erlenmeyer flasks containing 100 ml medium 85 are inoculated with 50 μl spore suspension. After incubation for 3–5 days at 24° and at 180 rpm in a circulatory agitating machine, a thick preculture is obtained.

(c) Main culture

The main stage is inoculated with 10% of the preliminary stage and incubated at 24° and at 180 rpm for 18 days in a 2 l Erlenmeyer flask with 1 liter of SL medium (composition and preparation: glucose 100 g/l, malt extract 0.4 g/l, yeast extract 0.4 g/l, $NH_4NO_3$ 0.4 g/l, $KH_2PO_4$ 0.4 g/l, $MgSO_4.7H_2O$ 0.4 g/l, demineralised water 1 l, sterilisation 120°, for 20 minutes).

EXAMPLE 2

CULTURE OF THE STRAIN NRRL 15684 IN A FERMENTER (a) Preculture

The first preliminary stage takes place in 2 l Erlenmeyer flasks containing 1 l of medium 85, each inoculated with 0.5 ml of spore suspension. Incubation for 5 days at 24°, at 180 rpm in a circulatory agitating machine.

(b) First intermediate culture

Two 75 l fermenters containing 50 l of medium 85 at 24°, with ventilation at a rate of 1 l/minute/liter medium, and stirring at 150 rpm with two disc stirrers of ϕ14 cm represent the first intermediate stage. This is inoculated at a rate of 10% with 5 l of the preliminary stage, and incubated for 5 days.

(c) Second intermediate culture

A 750 l fermenter containing 500 l of medium 85 and a 200 l fermenter containing 150 l of medium 85 form the second intermediate stage. Both are incubated for 3 days at 24°, at a ventilation rate of 1 l/minute/liter medium and are inoculated with 10% of the first intermediate stage. The 200 l fermenter is stirred at 100 rpm with 1 disc stirrer of ϕ35 cm and the 750 l fermenter is stirred at 100 rpm with 2 disc stirrers of 31 cm diameter.

(d) Main culture

The main stage in a 5 $m^3$ fermenter containing 3500 SL medium is inoculated with 350 l of the 750 l fermenter, ventilated at a rate of 1 l/minute/liter medium, incubated for 13 days at 24° and stirred at a peripheral velocity of the stirrer of 0.88m/s. The 2 $m^3$ main stage has the same peripheral velocity of the stirrer. It is filled with 1800 l of SL medium, inoculated with 180 l of the 200 l fermenter, and is also incubated for 13 days at 24° at a ventilation rate of 1 l/minute/liter medium.

The pH value in both main-stage fermentations is held around pH 6 by adding 4 N NaOH.

EXAMPLE 3

ISOLATION OF S 39163/F-I 10 l of culture broth are separated by a syrup filter into culture filtrate and mycelium. The culture filtrate obtained (ca. 8 liters) is then extracted three times, each with 4 liters of ethyl acetate, and the combined organic extracts are evaporated under vacuum. 4.7 g of crude extract are obtained.

The mycelium is broken down twice in an Ultra-Turrax, each time with 2 liters of methanol-acetone-water (45:45:10) and each time for 10 minutes. The combined extracts are then freed from acetone and methanol in a vacuum, and the remaining aqueous solution is extracted three times, each with 400 ml of ethyl acetate. After evaporation in vacuum, the organic phases yield 5.5 g of mycelium extracts. This crude extract is stirred out with methanol, whereby poorly-soluble, inactive impurities can be removed by filtration. The parts which are soluble in methanol are evaporated, and the residue combined with the crude extract from the culture filtrate. After dissolving in 90% aqueous methanol, and extraction three times, each with 100 ml of petroleum ether, the aqueous methanol extracts yield 6.67 g of crude product following evaporation in vacuum.

These 6.67 g scoured crude extracts from the culture filtrate and mycelium are dissolved in methanol, and the solution introduced onto a column of 1.1 kg Sephadex $LH_{20}$ in methanol. Elution with methanol at 50 ml per fraction, followed by evaporation in vacuum, yields 430 mg of material which contains S 39163/F-I. This fraction is dissovled in methylene chloride-methanol-water (78:20:2), and the solution introduced onto a column of 50 g silica gel Merck (grain size 0.05–0.2 mm) which is prepared with the same solvents. Elution throughout with methylene chloride-methanol-water (78:20:2) produces 145 mg of highly enriched metabolite. After taking up in methanol, filtration of the solution over talcum and evaporation in vacuum, analysis shows that pure S 39163/F-I is obtained (M.p. 126°–130° after 15 hours drying at room temperature under a high vacuum).

EXAMPLE 4

ISOLATION OF S 39163/F-I FROM A 5200 L FERMENTATION 5200 l of fermentation broth (obtained as in example 2) are separated at a pH of 6.0 using a Westfalia separator, whereby ca. 4500 liters of culture filtrate and ≈600 kg of mycelium are produced. The culture filtrate is then extracted twice in a counter-current extractor, each time with 2250 liters of ethyl acetate. The two extracts are concentrated to 620 liters at 75° in a vacuum in a Kühni gravity stream evaporator. The extract concentrate is then concentrated at 50° to ca. 5 liters under water ring vacuum in a Buchi and Schmid circulatory evaporator, and evaporated to dryness at 50° in a Büchi rotary evaporator. 1.057 kg of crude extract are obtained. The mycelium (ca. 600 kg) is homogenised three times in a Dispax reactor, each time with 700 liters of 90% methanol and each time for 1 hour. After separating the solid matter in a Westfalia separator, the methanolic extracts are combined, and whilst adding water, are concentrated to ca. 450 liters at a max. of 50° in a Büchi circulatory evaporator. This aqueous phase is then extracted three times, each time with 450 liters of ethyl acetate, and the extracts are washed, each time with 100 liters of water. The combined organic extracts are evaporated to dryness as above, and yield 1.380 kg of crude extract.

The two crude extracts of the culture filtrate and the mycelium (1.057 kg and 1.380 kg) are subsequently separated, dissolved in 10 times the amount of 90% methanol, and the solutions are extracted three times with an equal volume of hexane. After evaporation of the aqueous methanolic extracts, the following scoured crude extracts are obtained:

502 g of extract of the culture filtrate and resp. 630 g of extract of the mycelium.

The scoured crude extract of the culture filtrate (502 g) is subsequently dissolved in 3.2 liters of methanol, and this solution introduced onto 25 kg of Sephadex LH$_{20}$ in methanol (column diameter 30 cm). Elution with methanol yields 139 g of S 39163/F-I as a mixed fraction.

Similar gel filtration of 630 g of scoured crude extract of mycelium on Sephadex LH$_{20}$ produced 119.5 g of fractions containing S 39163/F-I. These two combined mixed fractions of S 39163/F-I from gel filtration (258.5 g) are dissolved in 1250 ml of toluene-isopropanol-water (50:50:5) and the solution introduced onto a column(diameter 15 cm) of 25 kg silica gel Merck 60 (grain size 0.040-0.063 mm) which is prepared with the same solvents. Elution throughout with toluene-isopropanol-water (50:50:5) yields 161.6 g of crude product of S 39163/F-I. This enriched preparation is subsequently chromatographed in portions on 100 times the amount of silica gel.

25 g of the crude preparation are then dissolved in 200 ml of methylene chloride-methanol-water (78:20:2), and the solution introduced onto a medium-pressure column of 2.5 kg of silica gel Merck 60 (grain size 0.04-0.063 mm) which is prepared with the same solvents. Elution takes place with methylene chloride-methanol-water (78:20:2) at a flow velocity of ca. 7 liters/hour. Following passage of 10 liters extracts appear containing S 39163/F-I.

Evaluation of chromatographic separation takes place after evaporation by means of thin-layer chromatographic analysis on silica gel Merck plates with methylene chloride-methanol-water (78:20:2) as the eluant. 15.7 g of S 39163/F-I are obtained which are uniform on thin-layer chromatographic analysis. A solution in methanol, after filtration over active carbon (Merck) and evaporation, yields S 39163/F-I as a colourless amorphous powder.

Pure S 39163/F-I is obtained from the crude preparation by means of chromatographic purification in portions on silica gel.

EXAMPLE 5

SODIUM SALT OF S 39163/F-I 2000 mg of S 39163/F-I are dissolved in ethylacetate and slowly mixed with 1.2 ml of a 10% methanolic sodium hydroxide solution, whereupon the sodium salt of S 39163/F-I precipitates. After filtering off or decanting the solution the sodium salt is recrystallized from methanol. For elementary analysis drying is carried out under high vacuum at room temperature.

Empirical formula: $C_{38}H_{59}O_9Na$ (MW 682.9)
Analysis: Found C, 66.7; H, 8.6; O, 21.4; Na, 3.36%.
Calc. C, 66.8; H, 8.7; O, 21.1; Na, 3.46%.
m.p. 195°–196° with decomposition
$[\alpha]_D^{20} = -23°$ (C=0.5 in MeOH).
$[\alpha]_D^{20} = -51°$ (C=0.45 in MzO).

We claim:
1. A compound of formula I

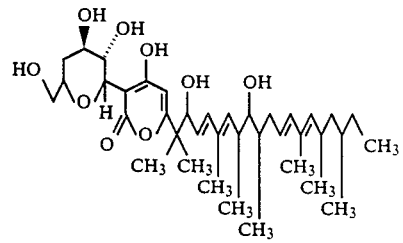

in free form or in the form of an alkali salt.

2. The metabolite S 39163/F-I according to claim 1 having the following approximate characterising features when in the form of a colourless amorphous powder:
   (i) m.p. 105°–115° sinterring, from 124° decomp.
   (ii) $[\alpha]_D^{20} = -15°$ (C=0.50 in methanol)
   (iii) empirical formula $C_{38}H_{60}O_9$
   (iv) molecular weight 660 (according to field desorption MS).
   (v) UV spectrum in methanol: Max. 205 nm, log $\epsilon'$1.69; 235 nm, log $\epsilon'$1.90; 290 nm, log $\epsilon'$1.18; (compare FIG. 1)
   (vi) IR spectrum $CH_2Cl_2$ (compare FIG. 2)
   (vii) $^1$H-NMR spectrum in dimethylsulphoxide, 360 MHz with tetramethylsilane as an internal standard (compare FIG. 3).

3. A pharmaceutical composition useful in treating diseases and infections caused by microbes and herpes viruses which comprises an anti-microbial or anti-herpes virus effective amount of a compound according to claims 1 or 2 in free form or in pharmaceutically acceptable alkali salt form in association with a pharmaceutically acceptable diluent or carrier.

4. A method of treating diseases and infections caused by microbes and herpes viruses which comprises administering to a subject in need of such treatment an anti-microbial or anti-herpes virus effective amount of a composition according to claims 1 or 2 in free form or in the form of a pharmaceutically acceptable alkali metal salt.

* * * * *